(12) United States Patent
Blacker et al.

(10) Patent No.: US 7,138,548 B2
(45) Date of Patent: Nov. 21, 2006

(54) PROCESS FOR THE PREPARATION OF ARYL HYDRAZONE AND ARYL HYDRAZINE

(75) Inventors: Andrew John Blacker, Huddersfield (GB); David Dodman, Huddersfield (GB); David Anthony Jackson, Bury (GB); Jan Michael Fielden, Huddersfield (GB); John Heathcote Atherton, Huddersfield (GB)

(73) Assignee: Avecia Limited, Manchester (GB)

( * ) Notice: Subject to any disclaimer, the term of this patent is extended or adjusted under 35 U.S.C. 154(b) by 93 days.

(21) Appl. No.: 10/493,503

(22) PCT Filed: Oct. 2, 2002

(86) PCT No.: PCT/GB02/04459

§ 371 (c)(1),
(2), (4) Date: Feb. 2, 2005

(87) PCT Pub. No.: WO03/035604

PCT Pub. Date: May 1, 2003

(65) Prior Publication Data

US 2005/0124824 A1 Jun. 9, 2005

(30) Foreign Application Priority Data

Oct. 23, 2001 (GB) .................................. 01254424

(51) Int. Cl.
*C07C 249/16* (2006.01)
*C07C 241/02* (2006.01)

(52) U.S. Cl. ...................................... 564/251; 564/314

(58) Field of Classification Search .................... None
See application file for complete search history.

(56) References Cited

U.S. PATENT DOCUMENTS 6,235,936 B1 * 5/2001 Buchwald et al. .......... 564/386

OTHER PUBLICATIONS

XP-002224949, Ref. 1 2034377; Journal; Bamberger; Frei; CHBEAM; Chem.Ber.; 35; 1902; 1092.
XP-002224950, Ref. 1, 2034406; Journal; Bamberger; CHBBEAM; Chem. Ber.; 31; 1898; 2632; Chem.Ber.; 34, 1901, 2004.
XP-002224951, Ref.1 2050690; Journal; Kratzl; Berger; MOCMB7; Monatsh. Chem.; 89; 1958; 83, 84, 86.
Hartwig, J.F., Angew, Chem. Int. Ed., 37(15):2090-2093 (1998).
Wagaw, et al., J. Am. Chem. Soc., 120(26):6621-6622 (1998).
Bailey, J. Amer. Chem. Soc., 47:167-174 (1925).
Bergbreiter, et al., "Comprehensive Organic Synthesis", 2:523-524 (1991).
Enders, et al., "Methoden der Organischen Chemie", Stickstoff Verbindungen 1, 10/2 (1967) pp. 310-312.

* cited by examiner

*Primary Examiner*—Brian Davis
(74) *Attorney, Agent, or Firm*—Morgan Lewis & Bockius-LLP

(57) ABSTRACT

A process for the preparation of a compound of formula (I):

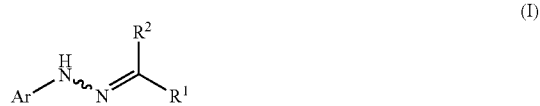

(I)

wherein Ar represents an optionally substituted aromatic carbocycle or heterocycle, and $R^1$ and $R^2$ independently represent hydrogen, $C_{1-10}$ alkyl, $C(O)C_{1-10}$ alkyl or optionally substituted aryl provided that $R^1$ and $R^2$ are not both hydrogen which process comprises reacting together a compound of formula (II):

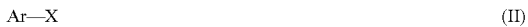

Ar—X (II)

wherein Ar is as defined in relation to formula (I) and X represents a leaving group with a a compound of formula (III)

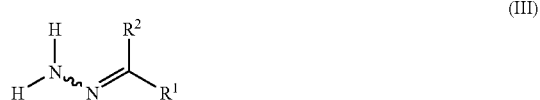

(III)

wherein $R^1$ and $R^2$ are as defined in relation to formula (I) under aqueous conditions in the presence of a Pd (II) salt, a ligand and a Group I or Group II metal hydroxide base at a pH greater than 7. Compounds of formula (I) may be hydrolysed to the corresponding hydrazine.

8 Claims, No Drawings

PROCESS FOR THE PREPARATION OF ARYL HYDRAZONE AND ARYL HYDRAZINE

This application is a 371 of PCT/GB02/04459 filed Aug. 2, 2002.

The present invention relates to a process for the preparation of aryl hydrazones and their use in making aryl hydrazines.

Aryl hydrazines are used widely as intermediates in agrochemical and pharmaceutical synthetic processes, particularly in the synthesis of compounds having heterocyclic rings.

In J. Am. Chem. Soc., (1998) 120, 6621–2 there is described the palladium-catalysed preparation of hydrazines under anhydrous conditions using bases that are incompatible with water. The use of such non-aqueous conditions results in a process that is expensive and makes effluent with a high chemical oxygen demand (COD). These factors make the process undesirable for large-scale manufacture of hydrazines.

According to the present invention there is provided a process for the preparation of a compound of formula (I):

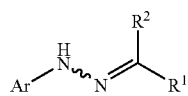
(I)

wherein Ar represents an optionally substituted aromatic carbocycle or heterocycle, and $R^1$ and $R^2$ independently represent hydrogen, $C_{1-10}$ alkyl, $C(O)C_{1-10}$ alkyl or optionally substituted aryl provided that $R^1$ and $R^2$ are not both hydrogen which process comprises reacting together a compound of formula (II):

Ar—X (II)

wherein Ar is as defined in relation to formula (I) and X represents a leaving group with a compound of formula (III):

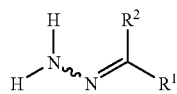
(III)

wherein $R^1$ and $R^2$ are as defined in relation to formula (I) under aqueous conditions in the presence of a Pd (II) salt, a ligand and a Group I or Group II metal hydroxide base at a pH greater than 7.

The expression "alkyl" refers to fully saturated straight or branched hydrocarbon chains having from one to ten, preferably one to six carbon atoms. Examples include methyl, ethyl, n-propyl, iso-propyl, n-butyl, t-butyl and n-hexyl. Expressions such as "alkoxy" and "haloalkyl" should be construed accordingly.

As used herein, the term "halogen" includes fluorine, chlorine, bromine and iodine.

Haloalkyl groups are alkyl groups which are substituted with one or more of the same or different halogen atoms and are, for example, $CF_3$, $CF_2Cl$, $CH_2CF_3$, $CH_2CH_2CF_3$, $CH_2(CF_2)_2CH_3$, $CH_2CHF_2$ or $CH_2CF_2CF_2CF_3$.

The reaction is preferably performed in the absence of air.

The reaction occurs in the aqueous phase but optionally an organic solvent may be added. Suitable organic solvents are hydrocarbons such as aromatic carbocycles for example methyl substituted benzenes, ethers such as tetrahydrofuran or alcohols such as methanol, ethanol and octanol.

Preferred organic solvents are aromatic carbocyclic hydrocarbons such as methyl substituted benzenes. A particularly useful organic solvent is toluene or xylene.

The compounds of formula (I) may be hydrolysed to aryl hydrazine compounds of formula (IV)

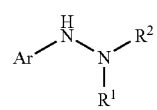
(IV)

wherein Ar, $R^1$ and $R^2$ are as defined in relation to formula (I). The hydrolysis is a standard organic transformation which can be performed by many methods such as hydrolysis with acids for example mineral acids. Suitable processes and conditions are those described in D E Bergbreiter & M Momongen, "Comprehensive Organic Synthesis" (1991), 2, 523–524 and in E. Enders, Houben-Weyl "Methoden der Organischen Chemie", Stickstoff Verbindungen I, 10/2 (1967), p310–312.

The process of the invention enables preparation of aryl hydrazones and aryl hydrazines using simple, inexpensive inorganic bases, under aqueous conditions, and is a relatively inexpensive process compared with that described in the prior art process which uses an expensive base (potassium t-butoxide) and which necessitates anhydrous conditions.

The reaction is applicable to a wide range of carbocyclic aryl groups. Typical aromatic carbocycle groups Ar and aryl groups $R^1$ and $R^2$ are ring systems that may be mono-, bi- or tricyclic. Examples of such rings include phenyl, naphthalenyl, anthracenyl or phenanthrenyl, preferably phenyl.

Typical aromatic heterocycle groups Ar are aromatic ring systems containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, and thiazolyl.

A preferred ring for Ar is phenyl.

When the groups $R^1$, $R^2$ and Ar are substituted, the substituents are one or more groups independently selected from alkyl, halogen, cyano, nitro, haloalkyl, amino, acylamino, $HO_2C$, $C_{1-6}$ alkoxy (itself optionally substituted by $C_{1-6}$ alkoxy), aryl($C_{1-4}$)alkoxy, $C_{1-6}$alkylcarbonyl, $C_{1-6}$alkoxycarbonyl, $C_{1-6}$alkylaminocarbonyl, di($C_{1-6}$ alkyl) aminocarbonyl, phenyl, halophenyl, $C_{1-6}$ alkylphenyl, $C_{1-6}$alkoxycarbonyl-phenyl, $C_{1-6}$ alkoxyphenyl, heteroaryl, aryloxy, arylcarbonyloxy, heteroaryloxy, heterocyclyl, heterocyclyloxy, $C_{3-7}$ cycloalkyl, $C_{3-7}$ cycloalkyloxy, $C_{5-7}$ cycloalkenyl and phosphonato groups where aryl and herteroaryl have the meanings as defined for Ar and heterocyclyl means a non-aromatic ring system containing at least one heteroatom and consisting either of a single ring or of two or more fused rings such as pyrrolidine, piperidine, thiomorpholine and morpholine each of which may be substituted by one or two independently selected ($C_{1-6}$) alkyl groups. Where a group has more than one substituent the substituents may be the same or different.

Preferred substituents for $R^1$, $R^2$ and Ar include $C_{1-8}$ alkyl, halogen, cyano, nitro, $C_{1-8}$haloalkyl, acylamino, and $C_{1-6}$ alkoxy (itself optionally substituted by $C_{1-6}$ alkoxy).

More preferred substituents for $R^1$, $R^2$ and Ar include $C_{1-6}$ alkyl, halogen, nitro, trifluoromethyl and $C_{1-6}$ alkoxy.

Preferably $R^1$ and $R^2$ are independently $C_{1-8}$ alkyl, phenyl or phenyl substituted by one or more of $C_{1-8}$ alkyl, halogen, cyano, nitro, $C_{1-8}$ haloalkyl, acylamino, and $C_{1-6}$ alkoxy (itself optionally substituted by $C_{1-6}$ alkoxy).

More preferably $R^1$ and $R^2$ are independently $C_{1-6}$ alkyl, phenyl or phenyl substituted by one or more of $C_{1-6}$ alkyl, halogen, nitro, trifluoromethyl or $C_{1-6}$ alkoxy.

Preferably Ar is phenyl or phenyl substituted by one or more of $C_{1-8}$ alkyl, halogen, cyano, nitro, $C_{1-8}$haloalkyl, acylamino, and $C_{1-6}$ alkoxy (itself optionally substituted by $C_{1-6}$alkoxy).

More preferably Ar is phenyl or phenyl substituted by one or more of $C_{1-6}$ alkyl, halogen, nitro, trifluoromethyl or $C_{1-6}$ alkoxy.

A preferred leaving group X is I, Br, Cl, —O-triflate or O-tosylate.

Suitable compounds that may be prepared by the invention include 3-trifluoromethyl-phenyl hydrazine, 4-methoxy-phenyl hydrazine, 4-nitro-phenyl hydrazine and 4-chloro-phenyl hydrazine.

Preferably, the base is sodium, potassium or lithium hydroxide or a hydroxide or oxide of magnesium, calcium or caesium.

The Pd (II) salt catalyst is preferably palladium chloride or palladium acetate.

Preferably the ligand is 2,2'-Bis(diphenylphosphino)-1,1'-binaphthyl (BINAP) either as a racemate or as (S)-(−)-2,2'-Bis(diphenylphosphino)-1,1-binaphthyl). The function of the ligand is to generate the catalytic species.

The reaction is preferably performed at a temperature of from 50° C. to 150° C.

More preferably the temperature is from 70° C. to 130° C., even more preferably 80° C. to 100° C.

The reaction may be operated at atmospheric pressure or at elevated pressure.

The ratio of compounds of formula (II to formula (III) is preferably from 3:1 to 1:3, more preferably 1.5:1 to 1:1.5, more preferably 1:1.

Preferably, the pH is greater than 9, more preferably greater than 10.

The invention will now be illustrated by way of example only. All parts and percentages are by weight unless otherwise stated.

EXAMPLE 1

This Example Illustrates the Preparation of N-(3-benzotriflouro)-benzophenone Hydrazone

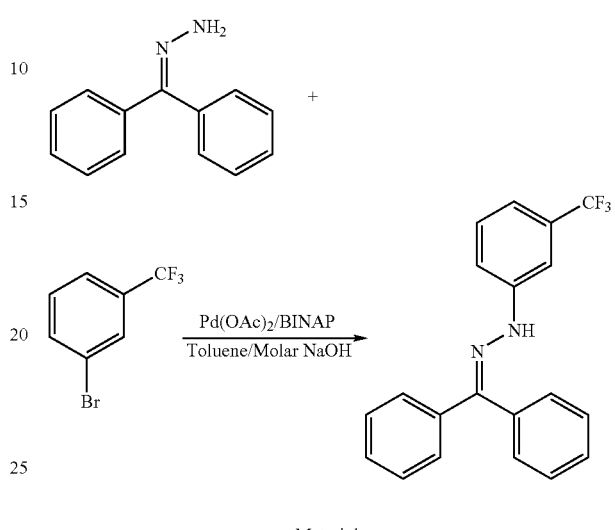

Materials

| MATERIAL | MWt | Weight Grams | 100% Wt Grams | Gram Mole | Molar Ratio |
|---|---|---|---|---|---|
| 3-bromobenzotrifluoride | 225 | 2.49 | 2.47 | 0.011 | 1.0 |
| Benzophenone hydrazone | 196 | 2.25 | 2.16 | 0.011 | 1.0 |
| (S)-(−)-BINAP | 622.7 | 0.128 | 0.124 | 0.0002 | 0.018 |
| Palladium acetate | 224.5 | 0.034 | 0.034 | 0.00025 | 0.023 |
| Toluene (degassed) | 92 | 15 mls | 13.0 | 0.141 | 12.84 |
| 1.0 Molar NaOH | 40 | 15 ml | 0.6 | 0.015 | 1.36 |

Toluene (15 mls; 13.0 gm) degassed with helium was charged to a dry nitrogen purged flask fitted with a nitrogen bubbler, stirrer and thermometer and the stirrer started. Palladium acetate (0.034 gms) and BINAP (0.124 gm) were added rapidly and stirred in to give a yellow solution. 3-Bromobenzotrifluoride (2.47 gm) was then added at ambient temperature and after stirring for 5 minutes benzophenone hydrazone (2.16 gm) was charged to the yellow solution causing it to turn to a dark red colour. Molar sodium hydroxide solution (15 mls.) degassed with helium was added and the resulting mixture heated to reflux (85–90° C.) over 20 minutes. The two-phase mixture was stirred at reflux for a total of about 8 hours by which time GC analysis showed that the reaction was complete. The reaction mixture was cooled to ambient temperature, transferred to a separating funnel and the lower aqueous phase separated off. The toluene layer was washed with water (10 mls) and evaporated under reduced pressure on a rotary evaporator to give the required hydrazone as a crude light brown viscous oil residue.

Weight of crude product=3.72 gm.

Strength (GC area %)=87.8%

Yield (based on GC Area % strength)=87.3%

EXAMPLE 2

This Example Illustrates the Preparation of N-(3-benzotriflouro)-benzophenone Hydrazone

| Material | Act. wt. g | Str. % w/w | 100% wt. g | MW | g moles | mol ratio |
|---|---|---|---|---|---|---|
| 3-bromobenzotrifluoride | 2.49 | 99 | 2.47 | 225 | 0.0110 | 1.00 |
| Benzophenone hydrazone | 2.25 | 98 | 2.21 | 196 | 0.0113 | 1.03 |
| Palladium acetate | 0.0351 | 98 | 0.0344 | 224.5 | $1.53 \times 10^{-4}$ | 0.0140 |
| Racemic-BINAP | 0.1307 | 98 | 0.128 | 622 | $2.06 \times 10^{-4}$ | 0.0188 |
| Sodium hydroxide sol$^n$ | 15 ml | 1.01 N | | 40 | 0.01515 | 1.38 |
| Toluene | 15 ml | 99.95 | | | | |

The palladium acetate, BINAP and toluene (previously degassed with helium) were charged to the reactor in a nitrogen atmosphere and the mixture was stirred for 10 minutes. The 3-bromobenzotrifluoride and benzophenone hydrazone were charged to the reactor. The aqueous sodium hydroxide solution (previously degassed with helium) was added and the mixture was heated to 90° C. and stirred at that temperature for 7.25 hours. The reaction mixture was cooled to room temperature and allowed to stand overnight. The reaction was continued the next day by heating to 90° C. After a further 7 hours, the mixture was cooled, 15 ml water was added to dissolve precipitated solid and the two phases were separated. The toluene phase was washed with water (15 ml) and the solvent was removed at 40° C. and reduced pressure on a rotary evaporator. The yield of product was 93%.

The experiment was repeated with 4-nitrobromobenzene, 4-methoxybromobenzene and 4-chlorobromobenzene using the same procedure as for 3-bromobenzotrifluoride.

The yield of hydrazone is shown below:

| Arylbromide | Yield of Hydrazone |
|---|---|
| 3-bromobenzotrifluoride | 93 |
| 4-nitrobromobenzene | 94 |
| 4-methoxybromobenzene | 2 |
| 4-chlorobromobenzene | 55 |

The invention claimed is:

1. A process for the preparation of a compound of formula (I):

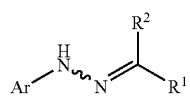

(I)

wherein Ar represents an optionally substituted aromatic carbocycle or heterocycle, and $R^1$ and $R^2$ independently represent hydrogen, $C_{1-10}$ alkyl, $C(O)C_{1-10}$ alkyl or optionally substituted aryl provided that $R^1$ and $R^2$ are not both hydrogen which process comprises reacting together a compound of formula (II):

Ar—X   (II)

wherein Ar is as defined in relation to formula (I) and X represents a leaving group with a compound of formula (III)

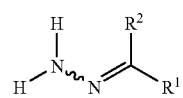

(III)

wherein $R^1$ and $R^2$ are as defined in relation to formula (I) under aqueous conditions in the presence of a Pd (II) salt, a ligand and a Group I or Group II metal hydroxide base at a pH greater than 7.

2. A process according to claim 1 which comprises the further step of hydrolysing a compound of formula (I) as defined in the claim to a compound of formula IV

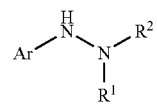

(IV)

wherein Ar, $R^1$ and $R^2$ are as defined in relation to formula (I).

3. A process according to claim 1 or claim 2 wherein Ar is optionally substituted phenyl.

4. A process according to claim 1 or claim 2 wherein $R^1$ and $R^2$ are independently $C_{1-8}$ alkyl, phenyl or phenyl substituted by one or more of $C_{1-8}$ alkyl, halogen, cyano, nitro, $C_{1-8}$ haloalkyl, acylamino, and $C_{1-6}$ alkoxy (itself optionally substituted by $C_{1-6}$ alkoxy).

5. A process according to claim 1 or claim 2 wherein the catalyst is palladium chloride or palladium acetate.

6. A process according to claim 1 or claim 2 wherein the ligand is 2,2'-bis(diphenylphosphino)-1,1'-binaphthyl or (S)-(−)-2,2'-bis(diphenylphosphino)-1,1'-binaphthyl).

7. A process according to claim 1 or claim 2 wherein the base is sodium, potassium or lithium hydroxide or a hydroxide or oxide of magnesium, calcium or caesium.

8. A process according to claim 1 or claim 2 wherein the pH is greater than 9.

* * * * *